United States Patent [19]
Ito et al.

[11] Patent Number: 4,822,774
[45] Date of Patent: Apr. 18, 1989

[54] PHYSIOLOGICALLY ACTIVE PEPTIDE

[75] Inventors: Osamu Ito, Sakura; Shinro Tachibana, Kashiwa, both of Japan

[73] Assignee: Eisai Co., Ltd., Tokyo, Japan

[21] Appl. No.: 177,998

[22] Filed: Apr. 5, 1988

Related U.S. Application Data

[62] Division of Ser. No. 35,125, Apr. 6, 1987, Pat. No. 4,757,133.

[30] Foreign Application Priority Data

Apr. 17, 1986 [JP] Japan ................................ 61-86987

[51] Int. Cl.$^4$ .............................................. A61K 37/02
[52] U.S. Cl. ...................................................... 514/12
[58] Field of Search ............................................ 514/12

[56] References Cited

U.S. PATENT DOCUMENTS

| | | | |
|---|---|---|---|
| 3,880,826 | 4/1975 | Said et al. | 530/324 |
| 4,016,258 | 4/1977 | Said et al. | 530/324 |
| 4,605,641 | 8/1986 | Bolin et al. | 530/324 |

Primary Examiner—Delbert R. Phillips
Assistant Examiner—Christina Chan
Attorney, Agent, or Firm—Flynn, Thiel, Boutell & Tanis

[57] ABSTRACT

A peptide is novel and useful for the bronchodilative activity and the hypotensive activity, having the following structure:

His-Ser-Asp-Ala-Val-Phe-Thr-Asp-Asn-Tyr-Thr-Arg-Leu-Arg-Lys-Gln-X-Ala-Val-Lys -Lys-Tyr-Leu-Asn-Ser-Ile-Leu-Asn-Gly-Y (wherein X is Met or Leu; and Y is OH, Lys-OH, Arg-OH, Lys-Arg-OH, or Lys-NH$_2$ when X is Met, or Y is Lys-NH$_2$, Lys-OH, or Lys-Arg-OH when X is Leu).

6 Claims, No Drawings

PHYSIOLOGICALLY ACTIVE PEPTIDE

This is a division of Ser. No. 035 125, filed Apr. 6, 1987, now U.S. Pat. No. 4,757,133.

The present invention relates to a novel physiologically active peptide having bronchodilative and hypotensive activities. Thus, the present invention is utilized in a field of drugs for medical treatment.

VIP (vasoactive intestinal polypeptide), which was isolated by S. Said et al., has an amino acid sequence analogous to those of secretin, glucagon and the like, and hence is classified as a peptide belonging to the glucagon family. Its physiological activities cover such a wide range that they are observed in many fields of, for example, the cardiovascular system, the respiratory system, the metabolic system, and the endocrine system. Recently, the function of VIP as a neurotransimitter has also attracted attention. The function of VIP in the respiratory system should be particularly noted. Specifically, VIP has a very strong function of relaxing the smooth muscles of a bronchus so that it can very well relax smooth muscles contracted by a stimulative substance such as acetylcoline, histamine, or serotonin. This relaxation function is characteristically different from those of ordinary bronchodilators, which act through the $\beta_2$-receptor of adrenaline, in that it is not inhibited by the $\beta$-blocker. This well suggests a possibility that VIP and its derivatives may exhibit a remarkable effect on a fit of intractable asthma on which a $\beta_2$-receptor stimulant does not effectively act. The following articles will be mentioned as documents describing the above-mentioned findings.

(a) S. Said, V. Mutt, Nature 225, 863 (1970).

(b) N. Hara, A. Guemei, S. Said et al., Clin. Res. 23, 347A (1975).

(c) Kudo, Sogo Rinsho 34 (11), 2497 (1985).

VIP is a peptide having an amidated C-terminal and consisting of 28 amino acids as represented by the primary structural formula which will be mentioned below. Since the content of VIP in vivo is low, a large amount of VIP cannot be obtained by extraction of a natural matter. The synthesis of the peptide by the liquid-phase or solid-phase process is so expensive that it may be difficult to put it into practice. Since the C-terminal is amidated, production of VIP by gene recombination is technically difficult and expensive.

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$

Under such circumstances, it is desired to provide a VIP derivative having VIP activities higher than those of VIP itself. Specifically, if such a VIP derivative has doubled activities, payability can be sufficiently secured even when it is prepared by the liquid-phase or solid phase process. In some cases, a possibility of inexpensive preparation of such a VIP derivative by gene recombination can be expected. In view of this, in the present invention, the problem to be solved by the invention is to provide a newly designed VIP derivative. VIP has a precursor of its own, the structure of which is revealed in the below-mentioned article (d). It is known that -Asn-Gly-Lys-Arg- in this structure undergoes several steps of enzymatic reactions to finally provide a C-terminal amide group, namely Asn-NH$_2$, of VIP. However, no intermediate products in the intermediate steps are known. Thus, there are no substances conceived as VIP derivatives. When the substance having an amide group at the C-terminal is converted into a substance having a carboxyl group at the C-terminal, the activities are generally notably lowered. However, what happens in the case of a VIP derivative is not elucidated. Under such circumstances, the inventors of the present invention have attempted to design a novel substance with a view to finding a VIP derivative having activities higher than those of VIP itself.

(d) N. Itoh, H. Okamoto et al.; Nature 304, 547 (1983).

As a result of investigations, usefulness was found in several newly designed substances. Certain designed substances have activities higher than those of natural VIP even though it has a carboxyl group at the C terminal. It was found that all the substances had a higher activity of relaxing the smooth muscles of a bronchus and/or a higher hypotensive activity than those of natural VIP.

The present invention has been completed based on such findings.

The present invention will now be described in detail.

The substance of the present invention is a novel peptide represented by a primary structural formula:

His-Ser-Asp-Ala-Val-Phe-Thr-Asp-Asn-Tyr-Thr-Arg-Leu-Arg-Lsy-Gln-X-Ala-Val-Lys-Lys-Tyr-Leu-Asn-Ser-Ile-Leu-Asn-Gly-Y (wherein X is Met or Leu; and Y is OH, Lys-OH, Arg-OH, Lys-Arg-OH, or LYs-NH$_2$ when X is Met, or Y is Lys-NH$_2$, Lys-OH, or Lys-Arg-OH when X is Leu). Here, -NH$_2$ stands for an amide group at the C-terminal, while -OH stands for a carboxyl group at the C-terminal.

The invention provides a process for synthesizing a peptide having the above defined, primary structure, which comprises the steps of attaching a C-terminal amino acid having been protected with a tertbutoxycarbonyl group at the N-terminal to a carrier through an amide group or an ester group, eliminating the tert-butoxycarbonyl group, condensing a second amino acid having a protective group on the N-terminal with the resulting C-terminal amino acid, then effecting the condensations one after another in sequence of the structure of the intended peptide with the subsequent amino acids, eliminating the protective groups from the peptide and taking the obtianed peptide out of the carrier.

The process may be followed by purifying the obtained peptide by the ion exchanging chromatography. It is preferred that the starting amino acid has a protective group on a reactive group of the side chain thereof.

Various novel designs in the present invention were made for the following reasons. Since VIP is produced from the known precursor through several steps of enzymatic reactions, a substance wherein X is Met and Y is OH, Lys-OH, or Lys-Arg-OH was designed as one conceived to be produced in the intermediate step. A substance wherein X is Met and Y is Arg-OH was designed as one having Arg directly bonded to Gly, which Arg is a basic amino acid like Lys, and a substance wherein X is Met and Y is Lys-NH$_2$ was designed as one having the C-terminal of a basic amino acid converted into an amide group to further increase the basicity, though they do not occur in nature.

Since Met at the 17th position of VIP is subject to oxidation so that inactivation due to oxidation is apprehended, substitution of Met in the 17th position with Leu which is resistant to oxidation was designed. Although such a sequence is not found in the natural substance, a substance wherein X is Leu and Y is Lys-OH, Lys-Arg-OH, or Lys-NH₂ was designed also in this case with consideration being given to the route of several steps of enzymatic reactions from the above-mentioned known precursor.

The substance of the present invention is confirmed by a peptide map after enzymatic decomposition and amino acid analysis values after hydrolysis. For further assuring identification, $[\alpha]_D$ and the retention time in HPLC as physical constants are shown in Table 1. The apparatus and conditions for measuring $[\alpha]_D$ are as follows:

apparatus: JASCO DIP-140 digital polarimeter manufactured by Nippon Bunko Co.
conditions: Na lamp 589 nm, temperature: 22° C.
  cell: 100 nm
  integration time: 5 sec
  concentration: 0.2 % (in 0.1 N acetic acid)
The column, solvent, detection, etc. in HPLC are as follows:
column: YMC ODS 5μ φ4.6 mm×L 250 mm
solvent: 0.1 % TFA-26.4 % CH₃CN-73.5 % H₂O
detection: 215 nm
conditions: 1.0 ml/min, isocratic/elution

TABLE 1

| X | Y | $[\alpha]_D^{22}$ | retention time (min) |
|---|---|---|---|
| Met | OH | −61.2 | 13.5 |
| | Lys—OH | −53.9 | 10.2 |
| | Arg—OH | −53.3 | 10.9 |
| | Lys—Arg—OH | −60.0 | 7.5 |
| | Lys—NH₂ | −52.9 | 8.8 |
| Leu | Lys—NH₂ | −52.8 | 11.1 |
| | Lys—OH | −56.3 | 12.4 |
| | Lys—Arg—OH | −54.9 | 8.9 |

The substance of the present invention can be synthesized by the known solid-phase or liquid-phase process. For example, it may be synthesized using a peptide Synthesizer Model 990B manufactured by Beckman by the solid phase process generally called the "Merrifield process."

A C-terminal amino acid involved in the substance of the present invention, which is protected with a tert-butoxycarbonyl group (hereinafter referred to briefly as "Boc") at the N-terminal, attached to a styrene resin is support through an amide or ester bond. Specifically, Boc-Gly, Boc-Lys (Cl-Z), or Boc-Arg (Tos) is bonded to, for example, a benzhydrylamine resin, a p-methyl-benzhydrylamine resin, or a chloromethyl resin. Subsequently, Boc is eliminated with an acid. An amino acid second from the C-terminal which is preliminarily protected at the N-terminal and, if necessary, at a functional group in the side chain is condensed with the above-mentioned amino acid to form a peptide bond. In this case, the protected amino acid is used in an amount of 3 to 5 times the theoretical amount. Dicyclohexylcarbodiimide (hereinafter referred to briefly as "DCC") or a mixture of DCC and 1-hydroxybenzotriazole (hereinafter referred to briefly as "HOBt") is used as the condensing agent. The completion of the reaction is confirmed by a point where the reaction of an amino group with ninhydrin becomes negative. In this manner, amino acids protected at the N-terminal and, if necessary, at a functional group in the side chain are sequentially condensed in accordance with the amino acid sequence in the primary structural formula of the substance of the present invention to finally obtain the substance of the present invention having both the functional group and the N-terminal protected. Finally, a treatment with hydrogen fluoride is conducted to eliminate the protective group and the resin from the substance of the present invention. In this treatment, anisole and dimethyl sulfide are added in order to prevent the side reaction. A crude product obtained by removing hydrogen fluoride may be purified by ion exchange chromatography using CM-cellulose or the like. The purity is confirmed by high performance liquid chromatography. If necessary, further purification may be effected by preparative high-performance liquid chromatography to obtain the substance of the present invention in purified form. Confirmation of the purity and the structure may be made by high-performance liquid chromatography, peptide map, amino acid analysis, etc.

The substances according to the present invention, which are VIP derivatives, have a higher activity of relaxing the smooth muscles of a bronchus and/or a higher hypotensive activity than those of VIP itself. Thus, the substances of the present invention have bronchodilative and hypotensive activities, and hence are expected to have usefulness thereof as an asthma treatment drug and a hypotensive drug in future. Since some of the derivatives have a carboxyl group at the C-terminal, they provide a possibility of mass production by gene recombination. Thus, they can be used in place of expensive VIP itself.

EXAMPLE 1

1.25 g of Boc-Lys(Cl-Z)-O-Resin (Boc-Lys(Cl-Z) content: 0.4 m mole/g, manufactured by Peninsula Labs.) was placed in a reaction vessel of a Peptide Synthesizer Model 990B manufactured by Beckman and stirred in CH₂Cl₂ for 2 hours to be swollen. Subsequently, Boc-Gly is reacted according to the procedure consisting of the following steps:

(1) washing three times with 20 ml of CH₂Cl₂;
(2) preliminarily washing with 20 ml of a CH₂Cl₂ solution of 40 % of TFA and 0.05 % of indole;
(3) deblocking with 20 ml of a CH₂Cl₂ solution of 40 % of TFA and 0.05 % of indole;
(4) washing three times with 20 ml of CH₂Cl₂;
(5) washing with 20 ml of MeOH;
(6) washing three times with 20 ml of CH₂Cl₂;
(7) preliminarily washing with 20 ml of a CH₂Cl₂ solution of 10 % of TEA;
(8) neutralizing with 20 ml of a CH₂Cl₂ solution of 10 % of TEA;
(9) washing three times with 20 ml of CH₂Cl₂;
(10) dissolving 2.5 m moles of a Boc-protected amino acid and 2.5 m moles of HOBt in a mixed liquid of 7.5 ml of DMF and 7.5 ml of CH₂Cl₂ and adding the resulting solution; and
(11) adding 5 ml of a 0.5M CH₂Cl₂ solution of DCC and conducting a reaction for 2 hours.

Introduction of Boc-Gly is completed by the above-mentioned procedure.

The steps (1) to (11) are repeated to form a peptide chain starting with sequence Gly toward an N-terminal.

The protected amino acids are added in the following order. Every amino acid was added in an amount of 2.5 m moles which is five times that of Lys bonded to the resin.

Boc-Asn 0.58 g/HOBt 0.34 g (The presence of HOBt improves the condensation yield and prevent racemization. However, when His is present, HOBt is not used because imidazole undergoes a change. In this case, 2.5 m moles of HOBt is added to every amino acid except for His which is a final N-terminal in coupling). Boc- Leu . H₂O 0.62g, Boc-Ile . ½H₂O 0.60 g, BOC-Ser(Bzl) 0.74 g, Boc-Asn 0.58 g, Boc-Leu . H₂O 0.62 g, Boc-Tyr(Br-Z) 1.24 g, Boc-Lys(Cl-Z) 1.00 g, Boc-Lys(Cl-Z) 1.00 g, Boc-Val 0.54 g, Boc-Ala 0.47, Boc-Leu . H₂O 0.62 g, Boc-Lys(Cl-Z) 1.00 g, Aoc-Arg(Tos) . ¼EtoAc . ½H₂O 1.18 g, Boc-Leu . H₂O 0.62 g, Aoc-Arg(Tos) . ¼EtoAc . ½H₂O 1.18 g, Boc-Thr(Bzl) 0.77 g, Boc-Tyr (Br-Z) 1.24, Boc-Asn 0.58 g, Boc-Asp(OcHex) 0.79 g, Boc-Thr(Bzl) 0.77 g, Boc-Phe 0.66 g, Boc-Val 0.54 g, Boc-Ala 0.47 g, Boc-Asp(OcHex) 0.79%, Boc-Ser (Bzl) 0.74 g, Boc-His(Tos) 1.03 g (HOBt is not added in this case)

When the above-mentioned procedure is completed, the following protected peptide is synthesized on the resin.

Boc-His(Tos)-ser(Bzl)-Asp(OcHex)-Ala(-)Val-Phe-Thr(Bzl)-Asp(OcHex)-Asn-Tyr(Br-Z)-Thr(Bzl)-Arg(Tos)-Leu-Arg(Tos)-Lys(Cl-Z)-Gln-Leu-Ala-Val-Lys(Cl-Z)-Lys(Cl-Z)-Tyr(Br-Z)-Leu-Asn-Ser(Bzl)-Ile(-)Leu-Asn-Gly-Lys(Cl-Z) resin.

This protected peptide attached to the resin is subjected to the aforementioned steps (1) to (9), filtered, and dried in a desiccator over night. 3.25 g of a dried protected peptide attached to the resin is obtained. 1.3 g thereof is treated with 30 ml of hydrogen fluoride in the presence of 2 ml of anisole and 0.5 ml of DMS at 0° C. for one hour. The hydrogen fluoride is distilled off. The residue is washed with a mixed liquid of anhydrous ether and n-hexane (1:1), washed with only anhydrous ether, and sufficiently dried. The peptide is dissolved in 50 ml of 10 % acetic acid, and the undissolved resin is filtered out. The obtained solution is filtered through a 0.22μ Millipore filter, followed by freeze drying. 628 mg of a crude peptide is obtained. Subsequently, the crude peptide is subjected to CM-cellulose column (2.5φ 30h cm), chromalography, and eluted (6.5 ml/fr) with AcONH₄ (pH: 7.0) having a straight line inclination ranging from 0.05 M to 0.5 M to elute the desired peptide in fr. No. 112 to 119. Thus, 104 mg of a partially purified peptide is obtained. It is then subjected to high-performance liquid chromatography under the following conditions:

column: YMC ODS 5μ φ10 mm×L 250 mm, solvent: R and S mentioned below are prepared, a solvent having a straight line inclination ranging from a mixed liquid of 65 % of R and 35 % of S to a mixed liquid of 40 % of R and 60 % of S is used:
R: $CH_3CN-H_2O$ (1:99, containing 0.1 % of TFA)
S: $CH_3CN-H_2O$ (6:4, containing 0.1 % of TFA),
rate of flow: 3 ml/min 10.0 mg of a pure peptide is obtained from 17.4 mg of the partially purified peptide by said chromatography. In this case, the yield is 8.5 % when calculated from coupling with Asn. The peptide map and amino acid analysis values are examined to confirm that the product is a substance according to the present invention. Further, the $[\alpha]_D^{22}$ and retention time are examined as values of physical properties. In this Example, the substance according to the present invention wherein X is Leu and Y is Lys-OH is obtained. The abbreviations used in the description are according to the nomenclature of IUPACIUB Commission [Eur. J. Biochem. 138, 9 (1984], and are as follows.

Bzl: Benzyl
Cl-Z: 2-Chlorobenzyloxycarbonyl
Tos: 4-Toluenesulfonyl
Br-Z: 2-Bromobenzyloxycarbonyl
OcHex: Cyclohexyl ester The results of amino acid analysis, conducted by the inventors of the present invention, of the substance obtained in this example are shown below for reference.

The hydrolysis reaction is conducted in 6N HCl (containing 0.1 % of phenol) at 110° C. for 20 hours, followed by analysis with a Hitachi amino acid analyzer Model 835. As described below, observed values well agrees with theoretical values, thus substantiating that the compound is a desired one according to the present invention.

| Amino acid | Theoretical value | Observed value |
| --- | --- | --- |
| Asp | 5 | 5.00 |
| Thr | 2 | 1.90 |
| Ser | 2 | 1.79 |
| Glu | 1 | 1.04 |
| Gly | 1 | 1.04 |
| Ala | 2 | 2.00 |
| Val | 2 | 2.00 |
| Ile | 1 | 0.95 |
| Leu | 4 | 4.00 |
| Tyr | 2 | 1.98 |
| Phe | 1 | 1.00 |
| Lys | 4 | 3.95 |
| His | 1 | 1.06 |
| Arg | 2 | 1.99 |

EXAMPLE 2

Substantially the same procedure as in Example 1 is repeated until completion of sequential introduction of protected amino acids except that 1.25 g of Boc-Met is used instead of 0.62 g of Boc-Leu.H₂O introduction of the 17th amino acid from the N-terminal.

When the procedure is fully completed, the following protected peptide is synthesized on the resin.

Boc-His(Tos)-Ser(Bzl)-Asp(OcHex)-Ala-Val-Phe-Thr(Bzl)-AsP(OcHex)-Asn-Tyr(Br-Z)-Thr(Bzl)-Arg(Tos)-Leu-Arg(Tos)-Lys(Cl-Z)-Gln-Met-Ala-Val-Lys(Cl-Z)-Lys(Cl-Z)-Tyr(Br-Z)-Leu-Asn-Ser(Bzl)-Ile-Leu-Asn-Gly-Lys(Cl-Z) resin.

After the aforementioned steps (1) to (9) are performed, the protected peptide attached to the resin is filtered and dried in a desiccator over night. 3.4 g of the dried protected peptide is obtained. 1.7 g of the dried protected peptide is treated with 30 ml of hydrogen fluoride in the presence of 2 ml of anisole and 0.5 ml of DMS at 0° C. for one hour. The hydrogen fluoride is distilled off, and the residue is washed with a mixed liquid of anhydrous ether and n-hexane (1:1), washed with only anhydrous ether, and sufficiently dried. The peptide is dissolved in 50 ml of 10 % acetic acid, and the undissolved resin is filtered out. The obtained solution is filtered through a 0.22μ Millipore filter, followed by freeze drying. 834 mg of a crude peptide is obtained. Subsequently, the crude peptide is subjected to CM-cellulose column (2.5φ×30h cm) chromatography, and eluted (6.5 ml/fr) with AcONH₄ (pH: 7.0) having a straight line inclination ranging from 0.05 M to 0.5 M to elute the desired peptide in fr. No. 109 to 121. Thus, 303 mg of a partially purified peptide is obtained. It is then subjected to high-performance liquid chromatography under the following conditions:

column: YMC ODS 5 μ φ 10 mm×L 250 mm, solvent: R and S mentioned below are prepared, a solvent having a straight line inclination ranging from a mixed liquid of 65 % of R and 35 % of S to a mixed liquid of 40 % of R and 60 % of S is used:
R: CH$_3$CN—H$_2$O (1:99, containing 0.1 % of TFA)
S: CH$_3$CN—H$_2$O (6:4, containing 0.1 % of TFA),
rate of flow: 3 ml/min.

11.5 mg of a pure peptide is obtained from 16.3 mg of the partially purified peptide by said chromatography. In this case the yield is 24.3 % when calculated from coupling with Asn. The peptide map and amino acid analysis values are examined to confirm that the product is a substance according to the present invention. Further, the $[\alpha]_D$ and retention time are examined as values of physical properties. In this Example, the substance according to the present invention wherein X is Met and Y is Lys-OH is obtained. The abbreviations in the description are the same as in Example 1.

The results of amino acids analysis, conducted by the inventors of the present invention, of the substance obtained in this Example are shown below for reference.

The hydrolysis reaction is conducted in 6N HCl (containing 0.1 % of phenol) at 110° C. for 20 hours, followed by analysis with a Hitachi amino acid analyzer Model 835. As described below, observed values well agrees with theoretical values, thus substantiating that the compound is a desired one according to the present invention.

| Amino acid | Theoretical value | Observed value |
|---|---|---|
| Asp | 5 | 5.00 |
| Thr | 2 | 1.94 |
| Ser | 2 | 1.80 |
| Glu | 1 | 1.06 |
| Gly | 1 | 1.06 |
| Ala | 2 | 2.05 |
| Val | 2 | 2.00 |
| Ile | 1 | 1.00 |
| Leu | 3 | 3.07 |
| Tyr | 2 | 2.02 |
| Phe | 1 | 1.01 |
| Lys | 4 | 3.98 |
| His | 1 | 1.07 |
| Arg | 2 | 2.02 |
| Met | 1 | 1.03 |

The effects of the present invention will now be shown by the following Experimental Example.

EXPERIMENTAL EXAMPLE

Samples

The substance of the present invention is used as a specimen. A natural VIP (hereinafter referred to briefly as "VIP-NH$_2$") and a synthetic VIP derivative (hereinafter referred to briefly as "VIP-OH") in which the C-terminal amide group of VIP has been substituted with a carboxyl OH group are prepared and used as control samples.

Methods

The following two determinations, A and B, are conducted.

A. Determination on Relaxation of Muscle of Bronchus Removed from Guinea Pig The juglar vein of a male guinea pig weighing 300 g or more is cut, causing the guinea pig to be bled to death. The guinea pig undergoes thoracotomy. Immediately after the thoracotomy, 3 cm of the trachea is taken out. The trachea is immediately put in a Krebs solution. It is then cut into seven equal rings, and the cartilages are connected to one another with a cotton yarn to form a chain. Subsequently, the smooth muscle parts and cartilages opposite them are cut, so that the smooth muscle parts can be connected to one another. The preparation thus prepared is placed in an isothermic glass cell having an internal capacity of about 7 ml and suspended from above. The lower part of the preparation is fixed, while the upper part is connected to an isometric transducer, to which 0.5 g of a load has been applied, in order to determine the relaxation reaction. Sufficient amounts of 95 % oxygen and 5 % carbon dioxide gas are blown into the preparation. Further, a Krebs solution of 37° C. containing $6.5 \times 10^{-6}$ M histamine is dropped on the preparation from above at a flow rate of 3.3 ml/min. The relaxation reaction takes place to an extent proportional to the amount of a sample added to the dropped solution. By utilizing this relationship, the relaxation activity against bronchial smooth muscle with respect to the substance of the present invention is compared with that of VIP—NH$_2$. VIP—NH$_2$ is used at a concentration of $10^{-5}$ M and dropped in amounts of 40 μl and 80 μl. The substance of the present invention is also used at a concentration of $10^{-5}$ M and dropped in amounts of 10 μl and 20 μl. The value of the area (height × time) in relaxation of each case is determined. The specific activities are obtained by taking the area value of VIP—NH$_2$ as 100 % and determining the relative ratio of the area value of each use. Thus, the relaxation reactions are compared by the four-point assay method, with respect to the above-mentioned determination method, reference may be made to the following articles (e) and (f):

(e) W. L. M. Perry, Pharmacological Experiments on Isolated Preparations: E & S Livingstone LTD. 1968; and (f) Castillo, De Beer, J. Phamac. Exp. Ther. 90, 104 (1947).

B. Determination of Carotid Artery Pressure on Rat

An SD male rat having a body weight of 200 g is anesthetized by intraperitoneally admininstering 48 % urethane at a dosage of 2.7 ml/kg. In order to inject the rat, cannulation is made to the carotid artery. The cannulation of a transducer for determining the blood pressure is also made to the carotid artery. A sample of 12.5 pmol/kg to 400 pmol/kg is administered into the carotid artery, and the change in blood pressure is plotted with a polygraph to obtain a dose-response curve. The amount of the sample required to produce a drop of 15 mmHg in blood pressure is determined from the curve. The required amount of VIP-NH$_2$ is taken as 100 %, and the specific activity of each sample is obtained by calculating the relative ratios.

With respect to the above-mentioned determination method, reference may be made to the following article (g):

(g) Suzuki, Araki, and Tachibana, Yakugaku Zasshi, 99 (2), 172 (1979).

Results

The results are shown in Table 2. In the Table, the value in col. A is the specific activity (%) obtained by the above-mentioned method A, while the value in col. B is the specific activity (%) obtained in the above-mentioned method B. As can be seen from Table 2, the substance of the present invention has a higher activity of relaxing the smooth muscle of a bronchus and/or and a higher hypotensive activity than those of the natural VIP.

TABLE 2

| Sample | X | Y | A | B |
|---|---|---|---|---|
| Specimen | Met | OH | 70 | 110 |
| | | Lys—OH | 300 | 200 |
| | | Arg—OH | 220 | 250 |
| | | Lys—Arg—OH | 460 | 180 |
| | | Lys—NH$_2$ | 140 | 80 |
| | Leu | Lys—NH$_2$ | 300 | 100 |
| | | Lys—OH | 410 | 220 |
| | | Lys—Arg—OH | 410 | 80 |
| Control | | VIP - NH$_2$ | 100 | 100 |
| | | VIP - OH | 60 | 70 |

What is claimed is:

1. A method of treating a patient afflicted with asthma which comprises administering to said patient a therapeutically effective amount of a peptide having the primary structural formula:

His-Ser-Asp-Ala-Val-Phe-Thr-Asp-Asn-Tyr-Thr-Arg-Leu-Arg-Lys-Gln-X-Ala-Val-Lys-Lys-Tyr-Leu-Asn-Ser-Ile-Leu-Asn-Gly-Y in which X is Met and Y is OH, Lys-OH, Arg-OH, Lys-Arg-OH or Lys-NH$_2$ or X is Leu and Y is Lys-NH$_2$, Lys-OH or Lys-Arg-OH.

2. A method as claimed in claim 1, in which X is Met and Y is OH, Lys-OH, Arg-OH, Lys-Arg-OH or Lys-NH$_2$.

3. A method as claimed in claim 1, in which X is Leu and Y is Lys-NH$_2$, Lys-OH or Lys-Arg-OH.

4. A method of treating a patient afflicted with hypertension which comprises administering to said patient a therapeutically effective amount of a peptide having the primary structural formula:

His-Ser-Asp-Ala-Val-Phe-Thr-Asp-Asn-Tyr-Thr-Arg-Leu-Arg-Lys-Gln-X-Ala-Val-Lys-Lys-Tyr-Leu-Asn-Ser-Ile-Leu-Asn-Gly-Y in which X is Met and Y is OH, Lys-OH, Arg-OH, Lys-Arg-OH or Lys-NH$_2$ or X is Leu and Y is Lys-NH$_2$, Lys-OH or Lys-Arg-OH.

5. A method as claimed in claim 4, in which X is Met and Y is OH, Lys-OH, Arg-OH, Lys-Arg-OH or Lys-NH$_2$.

6. A method as claimed in claim 4, in which X is Leu and Y is Lys-NH$_2$, Lys-OH or Lys-Arg-OH.

* * * * *